(12) United States Patent
Billig et al.

(10) Patent No.: US 7,294,317 B2
(45) Date of Patent: Nov. 13, 2007

(54) EXOTHERMIC REACTION SYSTEM

(75) Inventors: Barry Billig, Irvington, NY (US); Bhupendra Ranibhai Baria, Princeton Junction, NJ (US)

(73) Assignee: SD Lizenzverwertungsgesellschaft mbH & Co., Munich (DE)

( * ) Notice: Subject to any disclaimer, the term of this patent is extended or adjusted under 35 U.S.C. 154(b) by 370 days.

(21) Appl. No.: 09/779,030

(22) Filed: Feb. 8, 2001

(65) Prior Publication Data

US 2002/0106316 A1   Aug. 8, 2002

(51) Int. Cl.
*B01J 19/00* (2006.01)

(52) U.S. Cl. .................. 422/198; 422/188; 422/196; 422/197; 422/201; 422/202; 422/211; 422/222; 422/234; 422/236

(58) Field of Classification Search ............... 422/188, 422/196–198, 201, 202, 211, 222, 234, 236
See application file for complete search history.

(56) References Cited

U.S. PATENT DOCUMENTS

| | | | |
|---|---|---|---|
| 2,042,220 A | * | 5/1936 | Groll et al. ............... 568/471 |
| 2,383,711 A | * | 8/1945 | Clark et al. .............. 568/400 |
| 3,146,075 A | | 8/1964 | Robb et al. ................ 23/288 |
| 4,061,659 A | | 12/1977 | Nielsen et al. |
| 4,101,287 A | | 7/1978 | Sweed et al. ............ 23/288 K |
| 4,778,882 A | | 10/1988 | Oka et al. ................ 536/124 |
| 4,847,393 A | * | 7/1989 | Langley .................... 549/523 |
| 4,882,444 A | | 11/1989 | Dobson et al. ........... 549/534 |
| 4,921,681 A | | 5/1990 | Ozero et al. |
| 4,973,777 A | | 11/1990 | Alagy et al. ............. 585/403 |
| 5,114,685 A | * | 5/1992 | Sapoff ..................... 422/219 |
| 5,292,904 A | | 3/1994 | Sawada et al. |
| 5,504,052 A | | 4/1996 | Rizkalla et al. |
| 5,646,087 A | | 7/1997 | Rizkalla et al. |
| 5,691,269 A | | 11/1997 | Rizkalla |
| 5,854,167 A | | 12/1998 | Rizkalla et al. |

FOREIGN PATENT DOCUMENTS

| | | |
|---|---|---|
| CA | 1022178 | 6/1977 |
| GB | 898374 | 6/1962 |
| GB | 1103441 | 2/1968 |
| GB | 1449091 | 9/1976 |

OTHER PUBLICATIONS

Kasatkin, A.G. "Main Chemical Technology Processes and Apparatuses." Moscow, 1973, p. 327.

* cited by examiner

*Primary Examiner*—Basia Ridley

(57) ABSTRACT

A reactor and heat exchanger assembly is provided with the heat exchanger integrally affixed to the reactor exit head and adapted to immediately cool reactor gases from the reactor.

8 Claims, 1 Drawing Sheet

EXOTHERMIC REACTION SYSTEM

BACKGROUND OF THE INVENTION

1. Field of the Invention

The present invention relates to a reactor and cooler assembly which is useful for conducting exothermic reactions such as the reaction of molecular oxygen and ethylene to form ethylene oxide.

2. Description of the Prior Art

The oxidation of ethylene to form ethylene oxide is conventionally carried out in a shell and tube reactor. An appropriate solid catalyst comprised of silver is placed in elongated tubes and the reaction gases are passed at reaction conditions into contact with the catalyst. A circulating fluid is provided on the shell side to remove heat generated by the exothermic reaction.

It is important that the reaction gas mixtures be rapidly cooled after completion of the desired reaction in order to minimize the possibility of complete oxidation as well as undesirable side reactions such as formation of formaldehyde and/or acetaldehyde; the formation of such products causes purification problems since they are difficult to separate from product ethylene oxide.

The prior art has recognized this problem and among the suggested remedies has been the use of the last section of the reactor tubes to accomplish cooling of the reactor gases. U.S. Pat. No. 4,061,659 has suggested that a cooling zone be provided adjacent to the reaction zone, the cooling zone being filled with an inert refractory particulate having a surface area of 0.1 $m^2$/g or less.

British patent 1,449,091 provides a tubular reactor which is divided into three distinct zones. The reaction gases pass through tubes which in a first section are packed with inerts to provide a preheat zone, in a second section the tubes are packed with catalyst to provide a reaction zone, and these same tubes in a third section are packed with inert or are unpacked to provide a cooling zone.

U.S. Pat. No. 4,921,681 provides a tubular reactor forming a preheat, reaction, and cooling zone.

More recent U.S. Pat. No. 5,292,904 likewise describes a tubular reactor with the tubes divided into a preheat zone, a reaction zone and a final packed cooling zone.

SUMMARY OF THE INVENTION

In accordance with the present invention an improved reactor and cooler assembly is provided which is less costly to fabricate and operate, and which provides for rapid cooling of reaction gases. A tubular reactor of a conventional type is provided in conjunction with a heat exchanger which is integral with the discharge head of the tubular reactor and adapted to cool reaction gases.

BRIEF DESCRIPTION OF THE DRAWING

The attached drawing is a schematic representation of the reactor and cooler assembly of the invention.

DETAILED DESCRIPTION

Figure 1:
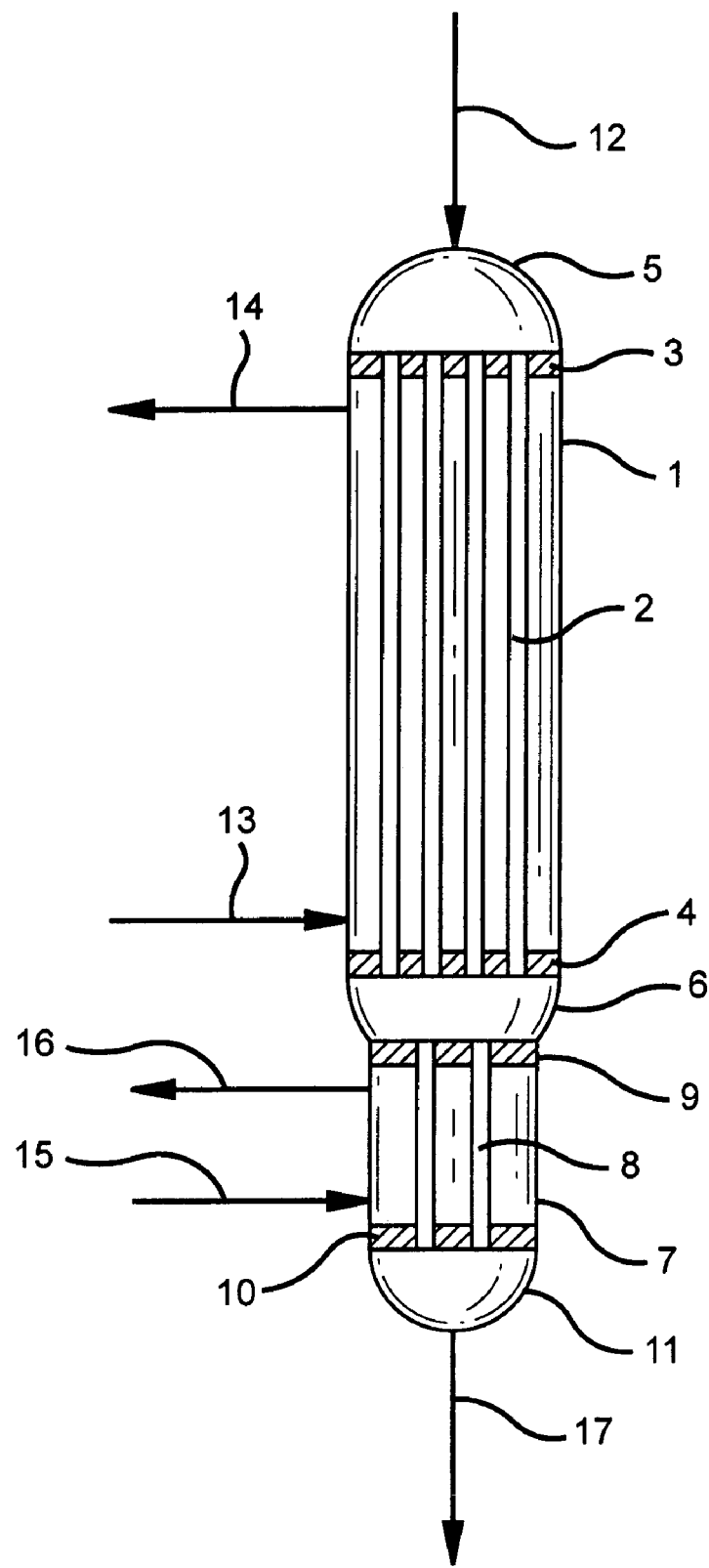

Referring to the drawing, reactor 1 is a shell and tube reactor of the type which is conventionally employed for ethylene oxide production. A multiplicity of elongated tubes 2 are provided in the reactor, the inlet ends being affixed to tube sheet 3 and the outlet ends to tube sheet 4. Inlet reactor head 5 is provided as is exit reactor head 6.

Shell and tube heat exchanger 7 is affixed to and integral with the exit reactor head 6, an opening is provided in exit head 6 for communication with heat exchanger 7 and conveniently heat exchanger 7 is welded to the exit head 6 around the opening thus forming an integral structure with the reactor. Heat exchanger 7 is provided with tubes 8 which are affixed to tube sheets 9 and 10 as indicated. Heat exchanger exit head 11 is provided.

As is illustrated in FIG. 1, the heat exchanger 7 is coaxially affixed to and integtal with the exit reactor head 6 of the reactor 1. As is also illustrated in FIG. 1, the heat exchanger tubes 8 within the heat exchanger 7 do not penetrate into the reactor 1.

In practice, reaction gases, eg. ethylene, oxygen and ballast gas are introduced into reactor 1 via line 12 and pass at reaction conditions through reactor tubes 2 which are packed with an appropriate silver catalyst. Heat of reaction is removed by a circulating heat transfer fluid such as water which is introduced via line 13 to the shell side of reactor 1 and removed via line 14.

Reaction gases pass through tubes 2 where production of ethylene oxide takes place and upon exiting tubes 2 the gases pass to exit head 6 and then to tubes 8 of exchanger 7 and are immediately cooled to prevent further oxidation and isomerization. A cooling fluid is introduced to the shell side of cooler 7 via line 15 and removed via line 16. Water is an appropriate and preferred cooling fluid. Cooled product gases exit cooler 7 via line 17 and are treated in a conventional fashion for the recovery of product and recycle of various components.

One of the advantages of the reactor and cooler assembly of the invention is that heat exchanger 7 can be expressly designed for maximum effectiveness in cooling the reaction gases without the constraints imposed by prior proposals where the reactor tubes are used for the cooling function. Flow rates, temperatures, and the like are separately regulated for the heat exchanger 7 independent of reactor 1 heat removal.

Heat exchanger tubes 8 can be packed with inert solid but preferably are not packed with solid materials.

Affixing the heat exchanger directly to the reactor head enables efficient cooler design and excellent structural integrity and insures immediate cooling of reaction gases because of the proximity of the heat exchanger to the reactor.

The cooling in tubes 8 is independent of the operation conditions of reactor 1 as the heat transfer fluid in heat exchanger 7 is not limited to conditions of reactor I as is the case when a cooling zone is provided as an extension of tubes 2 of reactor 1. Therefore optimum conditions can be maintained in heat exchanger 7 throughout the catalyst life cycle as the conditions change in reactor 1.

In addition, by constructing the heat exchanger 7 as an integral part of reactor 1 the residence time in exit reactor head 6 is minimized, thus limiting the time for by-product formation as contrasted to conventional practice where a conduit is provided to convey reaction gases to a separate external heat exchanger.

The improved reactor and heat exchange cooler assembly of the invention is generally useful for exothermic reactions such as oxidations which take place in tubular reactors where the reactants are contacted with catalyst packed in reactor tubes in a shell and tube reactor. The oxidation of ethylene to ethylene oxide is an important example.

The reactors which comprise a portion of the assembly of this invention are of the type generally employed in the exothermic reaction technology such as the production of ethylene oxide. Conventionally, such reactors comprise an upper inlet head for the admission of reaction gases and an exit head for the exit of reaction product. Tube sheets are provided to support the multiplicity of tubes packed with the appropriate catalyst through which the reactant gases pass and in which the desired reaction takes place. In the case of ethylene oxide production, reactors having a diameter as large as 15 to 20 feet are conventional with thousands of reactant tubes, illustratively 20 thousand or more, being supported by the tube sheets in the reactor. Tube lengths can range as long as 40 feet, a range of 20 to 40 feet being illustrative, tubes outside diameter of 1 inch to 2 inches being illustrative. The heat transfer medium is provided to remove the exothermic heated reaction. Various fluids including water, dowtherm, and the like can be employed.

Essential to the assembly of the invention is the provision of a heat exchanger integral to the exit head of the tubular reactor with an opening in the exit head 6 around which the heat exchanger is affixed as by welding. In the drawing integrally connected heat exchanger is designated as heat exchanger 7. Generally the heat exchanger can range in diameter from about 4 feet to 8 feet and contains tubes supported by upper and lower tube sheets, the tubes ranging from 800 to about 3000 in number and from about 1 inch to about 1.75 inches in outside diameter. A heat exchange fluid is provided for the cooling of the heat exchanger tubes in order to rapidly reduce the temperature of the reaction mixture to a point below which further oxidation and/or the production of various by-products takes place. Preferably the heat exchanger fluid is water.

Conventional supported silver catalysts are packed in the reactor tubes. Suitable catalysts and condition for use are described, for example, in U.S. Pat. Nos. 5,504,052, 5,646,087, 5,691,269, 5,854,167 and the like the disclosures of which are incorporated herein by reference.

The reactor portion of the assembly is comprised of materials which are well known in this particular art. The heat exchanger portion preferably is made from carbon steel or duplex steel and the tubes contained therein are preferably open and unpacked although if desired inert packing such as alumina or the like can be employed.

Tubular reactors for use, for example, in the production of ethylene oxide and well known and such reactors can comprise the reactor portion of the instant assembly.

A specific example of an assembly of the present invention which is adapted for the oxidation of ethylene to form ethylene oxide is described in the attached FIGURE. The material of construction for reactor 1 and cooler 7 is carbon steel. The reactor has a diameter of 16.5 feet and contains tubes supported by tube sheets 3 and 4, the 8809 reactor tubes having a length of about 27 feet, each tube having an outside diameter of 1.5 inches.

Welded to the lower exit head 6 of reactor 1 is heat exchanger 7. The heat exchanger has a diameter of about 6 feet and a length of about 10 feet and is welded to a 5.7 ft diameter opening in head 6. Supported in exchanger 7 by tube sheets 9 and 10 are 1468 tubes which are open and contain no packed solid. The tubes have an outside diameter of 1.25 inches.

The cooling heat exchange fluid introduced by means of line 15 and removed by means of line 16 is water.

Generally speaking the reaction gases which exit from reactor 1 through head 6 are at a temperature in the range of 420° F. to 540° F. In accordance of use of the assembly of the present invention, these gases are almost instantly cooled to below the temperature at which further reaction takes place in heat exchanger 7, i.e. to 420° F. or lower. The reaction gases enter heat exchanger 7 at essentially the exit reaction temperature from reactor 1 and exit heat exchanger 7 by means of heat exchanger exit head 11 via line 17. In accordance with the practice of the invention, the reaction gas mixture exiting via line 17 is treated in accordance with known procedures for the separation and recovery of product and recycle of components of the mixture such as unreacted ethylene, oxygen and ballast gas. exchanger 7, i.e. to 420° F. or lower. The reaction gases enter heat exchanger 7 at essentially the exit reaction temperature from reactor 1 and exit heat exchanger 7 by means of exit head 11 via line 17. In accordance with the practice of the invention, the reaction gas mixture exiting via line 17 is treated in accordance with known procedures for the separation and recovery of product and recycle of components of the mixture such as unreacted ethylene, oxygen and ballast gas.

We claim:

1. A reactor and heat exchanger cooler assembly which is comprised of tubular reactor having an upper inlet head and a lower outlet head, reaction tubes packed with catalyst within said reactor supported by an inlet end tube sheet and an outlet end tube sheet, a tubular heat exchanger having an upper end and a lower end, and comprising upper and lower end tube sheets supporting tubes within said exchanger, the upper end of said exchanger being integrally affixed around an opening of the reactor lower outlet head thus forming an integral structure with the reactor, said opening of the reactor lower outlet head being for the passage of reaction gases from the reactor to said heat exchanger and through tubes in said heat exchanger whereby said reaction gases are cooled by indirect heat exchange with a heat exchange fluid introduced into said heat exchanger.

2. The assembly of claim 1 wherein means are provided for cooling the tubes in both the reactor and the heat exchanger with water.

3. The assembly of claim 1 wherein the reactor is packed with a supported silver catalyst.

4. The assembly of claim 1 wherein the heat exchanger comprises a fluid introduction line.

5. The assembly of claim 1 wherein the heat exchanger comprises a fluid removal line.

6. The assembly of claim 1 comprising at least 20 thousand reaction tubes, wherein the reaction tubes have a length of from 15 feet to 40 feet, and an outside diameter of 1 inch to 2 inches.

7. The assembly of claim 1 wherein the heat exchanger is welded around the opening of the reactor lower outlet head.

8. The assembly of claim 1 wherein the heat exchanger has a diameter of from about 4 feet to 8 feet and contains tubes ranging from 800 to about 3000 in number and from about 1 inch to about 1.75 inches in outside diameter.

* * * * *